(12) United States Patent
Mohamed Elmahdy et al.

(10) Patent No.: US 10,813,842 B2
(45) Date of Patent: *Oct. 27, 2020

(54) MEDICATION ADHERENCE MONITORING (71) Applicant: AT&T Intellectual Property I, L.P., Atlanta, GA (US)

(72) Inventors: Mohamed Ahmed Mohamed Elmahdy, Houston, TX (US); Shaoda Yu, Katy, TX (US); Nadia Morris, Houston, TX (US); Duane Michael Scott Johnson, Sandy, UT (US); Michael Osborne Isom, West Valley City, UT (US); Steven Todd Barth, Salt Lake City, UT (US)

(73) Assignee: AT&T INTELLECTUAL PROPERTY I, L.P., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/672,565

(22) Filed: Nov. 4, 2019

(65) Prior Publication Data

US 2020/0155416 A1 May 21, 2020

Related U.S. Application Data

(63) Continuation of application No. 16/195,172, filed on Nov. 19, 2018, now Pat. No. 10,463,574.

(51) Int. Cl.
*A61J 7/04* (2006.01)
*G16H 20/13* (2018.01)
(Continued)

(52) U.S. Cl.
CPC ............. *A61J 7/0436* (2015.05); *A61J 1/035* (2013.01); *A61J 7/0418* (2015.05); *A61J 7/0481* (2013.01);
(Continued)

(58) Field of Classification Search
CPC ........ A61J 7/0436; A61J 7/0418; A61J 1/035; A61J 7/0481; G16H 20/13
(Continued)

(56) References Cited

U.S. PATENT DOCUMENTS 4,616,316 A 10/1986 Hanpeter et al.
5,412,372 A 5/1995 Parkhurst et al.
(Continued)

FOREIGN PATENT DOCUMENTS

EP 2244684 B1 9/2013
EP 2243461 B1 10/2013
(Continued)

OTHER PUBLICATIONS

"eTYP Device," Shlomi Mir, shlomimir.com, Jul. 30, 2016. https://web.archive.org/web/20160730012550/https://www.shlomimir.com/etyp-device/.
(Continued)

*Primary Examiner* — Kerri L McNally (57) ABSTRACT

In one example, the present disclosure describes a device, computer-readable medium, and method for monitoring a patient's medication adherence. In one example, an apparatus includes a set of contact pins to electrically engage a conductive trace circuit of a unit dose packaging and to generate a signal in response to a break in the conductive trace circuit, a processor comprising a plurality of analog channels to detect and record the signal, a cellular modem to send, via a data network to which the apparatus is connected, information about the signal to a medication adherence monitoring service, a housing containing the set of contact pins, the processor, and the cellular modem, wherein the housing is configured for removable insertion of the unit dose packaging, and a lock to reversibly lock the unit dose packaging in the housing.

20 Claims, 6 Drawing Sheets

(51) Int. Cl.
*A61J 1/03* (2006.01)
*H04W 84/04* (2009.01)

(52) U.S. Cl.
CPC .......... *G16H 20/13* (2018.01); *A61J 2200/30* (2013.01); *H04W 84/042* (2013.01)

(58) Field of Classification Search
USPC ...................................................... 340/539.1
See application file for complete search history.

(56) References Cited

U.S. PATENT DOCUMENTS

| | | | |
|---|---|---|---|
| 6,529,446 | B1 | 3/2003 | De |
| 7,126,879 | B2* | 10/2006 | Snyder .................. A61J 7/0481 368/10 |
| 7,170,823 | B2 | 1/2007 | Fabricius et al. |
| 7,699,174 | B2 | 4/2010 | Allison et al. |
| 9,233,051 | B2 | 1/2016 | Tufi |
| 9,622,942 | B2 | 4/2017 | Maijala et al. |
| 9,717,653 | B2 | 8/2017 | Harris |
| 9,757,305 | B2 | 9/2017 | Ika et al. |
| 9,779,216 | B2* | 10/2017 | Siegel .................... G16H 20/13 |
| 9,919,861 | B2 | 3/2018 | Bolognia et al. |
| 9,931,278 | B2* | 4/2018 | Schmid .................. A61J 1/035 |
| 10,463,574 | B1* | 11/2019 | Mohamed Elmandy .................... A61J 7/0436 |
| 2001/0028308 | A1 | 10/2001 | De |
| 2005/0162979 | A1 | 7/2005 | Ostergaard et al. |
| 2008/0197043 | A1 | 8/2008 | Freeze et al. |
| 2008/0303665 | A1 | 12/2008 | Naik et al. |
| 2009/0065506 | A1* | 3/2009 | Currie .................. B65D 50/046 220/324 |
| 2009/0194434 | A1* | 8/2009 | Ellis ........................ A61J 1/035 206/1.5 |
| 2009/0259486 | A1 | 10/2009 | Burg et al. |
| 2016/0132661 | A1* | 5/2016 | Dixit ........................ A61J 1/16 206/531 |
| 2017/0248401 | A1* | 8/2017 | Isom ..................... A61J 7/0076 |
| 2017/0283151 | A1 | 10/2017 | Stormer et al. |
| 2017/0294105 | A1* | 10/2017 | Mehregany ............ G08B 21/24 |
| 2017/0312183 | A1 | 11/2017 | Wilson et al. |

FOREIGN PATENT DOCUMENTS

| | | |
|---|---|---|
| EP | 2906176 B1 | 7/2016 |
| WO | 2017219035 A1 | 12/2017 |

OTHER PUBLICATIONS

Lo, Chris, "The smart approach to pharma packaging," Pharmaceutical Technology, pharmaceutical-technology.com, Sep. 27, 2011. https://www.pharmaceutical-technology.com/features/featurethe-smart-approach-to-pharma-packaging/.

* cited by examiner

MEDICATION ADHERENCE MONITORING

This application is a continuation of U.S. patent application Ser. No. 16/195,172, filed Nov. 19, 2018, now U.S. Pat. No. 10,463,574, which is herein incorporated by reference in its entirety.

The present disclosure relates generally to healthcare, and relates more particularly to devices and methods for monitoring a patient's medication adherence.

BACKGROUND

Medications are used to diagnose, cure, treat, and/or prevent diseases and other health conditions. For instance, a healthcare patient may be instructed to regularly take a specific medication to manage a chronic condition (e.g., diabetes, arthritis, high blood pressure, etc.). In other cases, the patient may be instructed to take a specific medication for a defined period of time in order to treat a short-term condition (e.g., a bacterial or viral infection) or to prepare for other medical treatment (e.g., surgery).

SUMMARY

In one example, the present disclosure describes a device, computer-readable medium, and method for monitoring a patient's medication adherence. In one example, an apparatus includes a set of contact pins to electrically engage a conductive trace circuit of a unit dose packaging and to generate a signal in response to a break in the conductive trace circuit, a processor comprising a plurality of analog channels to detect and record the signal, a cellular modem to send, via a data network to which the apparatus is connected, information about the signal to a medication adherence monitoring service, and a housing containing the set of contact pins, the processor, the cellular modem, wherein the housing is configured for removable insertion of the unit dose packaging, and a lock to reversibly lock the unit dose packaging in the housing.

In another example, a method includes activating a lock that reversibly interfaces a unit dose packaging with a dock, detecting a malfunction of the lock, and reporting, over a cellular communications network, information relating to the malfunction to a remote medication adherence monitoring service.

In another example, an apparatus includes a processor and a computer-readable medium storing instructions which, when executed by the processor, cause the processor to perform operations. The operations include electronically activating a lock that reversibly interfaces a unit dose packaging with a dock, electronically monitoring a use of medication contained in the unit dose packaging by detecting breaks in a conductive trace circuit that is embedded in the unit dose packaging, and electronically deactivating the lock when the monitoring indicates that all expected doses of the medication have been removed from the unit dose packaging.

BRIEF DESCRIPTION OF THE DRAWINGS

The teachings of the present disclosure can be readily understood by considering the following detailed description in conjunction with the accompanying drawings, in which.

To facilitate understanding, identical reference numerals have been used, where possible, to designate identical elements that are common to the figures.

DETAILED DESCRIPTION

In one example, the present disclosure provides a device and method for monitoring a patient's medication adherence. As discussed above, medications are used to diagnose, cure, treat, and/or prevent diseases and other health conditions. Adherence to the medication's indicated regimen (i.e., intake at the proper times and in the proper dosages) is critical in order for the medication to work as intended. For instance, missing a scheduled dosage may prolong an illness, and taking more than the scheduled dosage may lead to additional health problems (e.g., overdose). In other cases, some healthcare insurance providers may require proof of medication adherence before approving coverage for medical procedures. However, it is often difficult to determine whether a patient is adhering to the indicated regimen until or unless evidence of failure to adhere becomes apparent. Typically, medications are prescribed by doctors at specific dosages and administered by pharmacies, but there are few feasible ways to monitor medication adherence once the medication is in the patient's control.

Examples of the present disclosure provide a dock that is capable of reading a "smart" unit dose packaging (also referred to as a "blister pack") containing individual, measured doses of a medication. The unit dose packaging includes an embedded conductive trace circuit that connects to at least one pocket (or "blister"). When the pocket is opened to dispense a dose of the medication, the conductive trace circuit is broken in a location corresponding to the pocket. The dock, which is interfaced with the unit dose packaging, scans the conductive trace circuit and detects when the conductive trace circuit is broken. In this way, the dock can quickly identify and record when a dose of the medication has been removed from the unit dose packaging (and presumably consumed by a patient). The dock may include a cellular modem or other communication interface that provides wireless cellular (e.g., 3G or 4G long term evolution) connectivity. This allows the dock to communicate with other devices, so that the consumption of the medication can be reported, so that reminders to take scheduled doses of medication can be sent to patients, or so that other actions can be taken.

Figure 1:
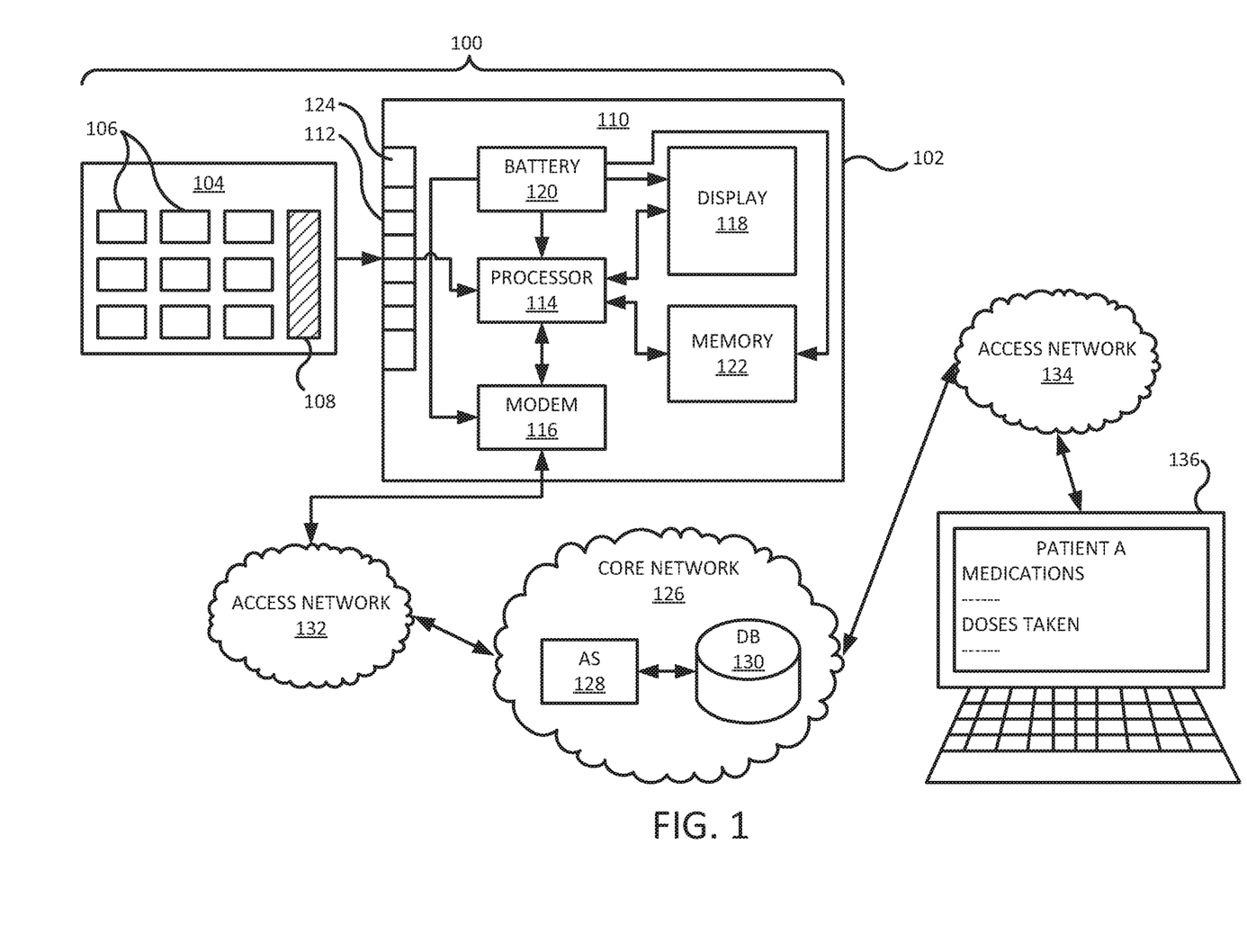
FIG. 1 illustrates an example system for monitoring a patient's medication adherence.

To further aid in understanding the present disclosure, FIG. 1 illustrates an example system 100 for monitoring a patient's medication adherence. In one example, the system 100 generally comprises a dock 102 and a unit dose packaging 104 with which the dock can interface.

The unit dose packaging 104 includes at least one pocket 106 which contains an individual dose of a medication (e.g., a tablet or pill). In the example illustrated in FIG. 1, the unit dose packaging 104 includes a plurality of pockets. For instance, the unit dose packaging 104 may contain a week's worth of doses of the medication, where each pocket contains one day's dose.

As discussed in further detail in connection with FIG. 2, the unit dose packaging also includes an embedded conductive trace circuit that connects to each pocket 106. A contact portion 108 of the conductive trace circuit is visible in FIG. 1. The contact portion 108 is sized to interface with contacts in the dock 102 as described in further detail below. In one example, the contact portion 102 is positioned near one end of the unit dose packaging 104.

Figure 3:
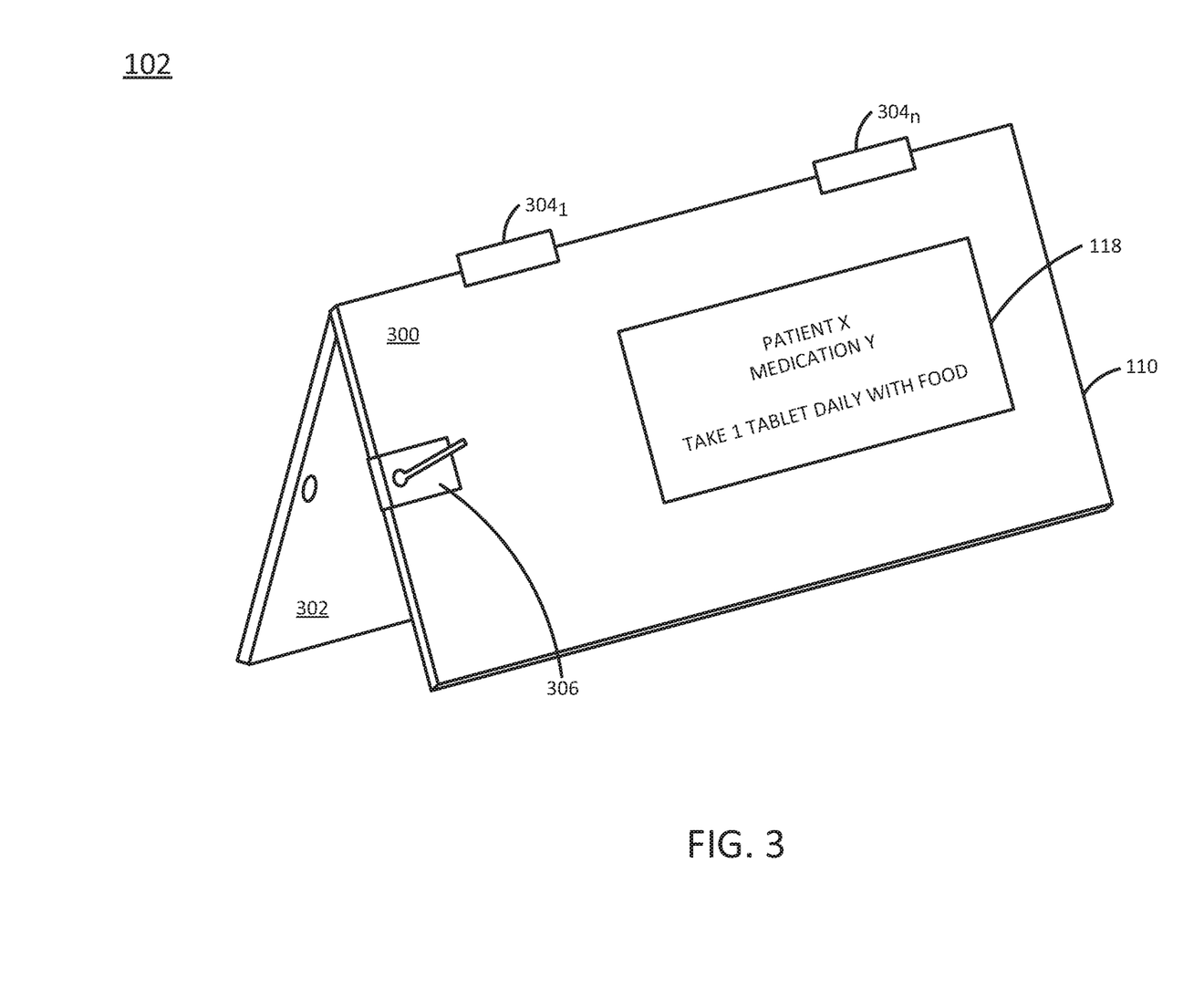
FIG. 3 illustrates one example of the dock illustrated in FIG. 1.

The dock 102 comprises a plurality of components contained within a housing 110. In one example, these components may include a set of contact pins 112, a processor 114, a modem 116, a display 118, a battery 120, and a memory 122. As illustrated in FIG. 3, which illustrates one example of the dock 102 illustrated in FIG. 1, in one example, the housing 110 may have a hinged or clamshell design that allows its interior and components housed within to be easily accessed (e.g., for maintenance, replacement, etc.). For instance, the housing 110 may include a first portion 300 and a second portion 302. The first portion 300 and the second portion 302 may have substantially similar (e.g., planar) shapes and dimensions. At least one hinge $304_1$-$304_n$ (hereinafter individually referred to as a "hinge 304" or collectively referred to as "hinges 304") may connect the first portion 300 of the housing 110 to the second portion 302 of the housing 110. The hinge(s) 304 may allow the first portion 300 of the housing 110 to rotate relative to the second portion 302 of the housing 110, so that the housing 110 may open and close. FIG. 3 illustrates the housing 110 in a partially open position. A fully closed position may bring the first portion 300 and the second portion 302 flush against each other (e.g., in a stacked orientation), while a fully open position may allow the first portion 300 and the second portion 302 to rest adjacent to each other (e.g., separated by the hinge(s) 304).

A hinged design such as that illustrated in FIG. 3 may also allow for insertion and/or removal of the unit dose packaging 104 (e.g., by opening up the housing 110, and then closing the housing 110 around the unit dose packaging 104). In one example, the housing further includes a lock 306 that reversibly locks the unit dose packaging 104 into place (e.g., so that the unit dose packaging 104 cannot be removed from the dock 102 unless one has the means to unlock the lock 306). For instance, engagement of the lock 306 may prevent rotation of the first portion 300 of the housing 110 away from the second portion 302 of the housing 110 (and thereby prevent opening of the housing 110). Conversely, disengagement of the lock 306 may allow rotation of the first portion 300 of the housing 110 relative to the second portion 302 of the housing 110 (and thereby allow opening of the housing 110). Thus, the lock 306 may be useful to ensure that only certain individuals having the proper key (e.g., a pharmacist or doctor) can open the housing 110. This may prevent tampering with the unit dose packaging 104 and/or the dock 102 and help to ensure that a patient's medication adherence data (e.g., as reported by the dock 102) is accurate. In some examples, the lock 306 may be communicatively coupled to the processor 114, so that the processor 114 can detect if the lock 306 is damaged or malfunctioning. Moreover, the lock 306 may be locked and unlocked manually (e.g., with a physical key) or electronically (e.g., by sending a command or password to the dock 102, possibly from an authenticated device).

Referring back to FIG. 1, the set of contact pins 112 is positioned within an opening 124 in the housing 110 and is further positioned to align with the contact portion 108 of the conductive trace circuit on the unit dose packaging 104 when the unit dose packaging 104 is inserted into the opening 124. This allows the set of contact pins 112 to continuously interface with or electrically engage the contact portion 108 of the conductive trace circuit and to generate signals in response to any breaks in the conductive trace circuit, where a break is assumed to indicate that the dose of medication contained in the pocket corresponding to the location of the break has been removed. In one example, at least one magnet (not shown) may be embedded in the housing to ensure proper interfacing of the set of contact pins 112 with the contact portion 108 of the conductive trace circuit. The set of contact pins 112 may be formed from a conductive material, such as gold or another metal, and may be spring loaded. In one example, the set of contact pins 112 includes at least twenty individual contact pins, although other numbers of contact pins may be used.

The set of contact pins 112 may be communicatively coupled to the processor 114, so that the processor 114 receives and interprets the signals that are generated by the set of contact pins 112. For instance, the processor 114 may determine, based on the signals generated by the set of contact pins 112, when the conductive trace circuit of the unit dose packaging 104 is broken. To this end, the processor 114 may comprise at least one analog channel or circuit to analyze the conductive trace circuit. In one example, the processor 114 is a microprocessor.

The processor 114 may send information regarding the doses that are dispensed to the display 118 for display on the dock 102, or to the modem 116 for transmission to a remote networked device or service. The processor 112 may also store this information locally, e.g., in the memory 122. This information may include, for example, the time at which a dose was dispensed, a number of doses dispensed, and/or other information.

The display 118 may comprise any type of display, such as an electronic ink (e-ink) thin film transistor (TFT) display, a touch screen display, or the like. In one example, the display 118 is an e-ink display that provides high visibility and a wide viewing angle for the information being displayed while consuming minimal power. In another example, the display 118 is a touch screen display that provides a graphical user interface (GUI) through which a user can control and interact with the dock 102. Such a GUI may be presented instead of or in addition to physical buttons or keys (or other user input devices) on the housing 110. In further examples, the dock 102 may include other output devices for providing output to a patient, such as a speaker to provide an audible alert or a mechanism for provide haptic feedback.

The modem 116 may comprise a cellular modem (e.g., a cellular chip modem). The modem 116 may further allow the dock 102 to connect to software and/or services running over a data network (e.g., to "the cloud"), for instance to retrieve information about medications, indicated regimens, other healthcare information. This information may be used to display feedback to a user, including, for example, reminders (e.g., when to take doses of the medication to ensure adherence to the medication's indicated regimen, when to order refills of the medication or schedule a follow up with a healthcare provider), instructions (e.g., when to contact a healthcare provider, for instance if there is more than a threshold inconsistency between the medication's indicated regimen and the number of doses of the medication that are dispensed), and other types of feedback related to medication adherence. The modem 116 may also allow the dock 102 to send or store information relating to doses of medication that are dispensed from the unit dose packaging 104, as discussed above.

The memory 122 may comprise a non-transitory computer-readable storage medium that stores instructions for execution by the processor 114. These instructions may cause the processor 114 to perform various operations related to monitoring a patient's medication adherence (e.g., including determining and/or reporting a number of doses of a medication that are assumed to have been dispensed, providing feedback on the number of doses, and other operations). The memory 122 may additionally be used to locally store information relating to doses of medication that are dispensed from the unit dose packaging 104, as discussed above.

The battery 120 may comprise a rechargeable or non-rechargeable (e.g., replaceable) power source that provides electrical power to at least some of the components of the dock 102. For instance, in FIG. 1, the battery 120 is connected to the processor 114, the modem 116, the display 118, and the memory 122. In one example, the battery 120 comprises a lithium ion battery, which may be recharged using a lithium-ion polymer (LiPo) charge circuit and boost converter.

The system 100 may connect (e.g., via the modem 116) to a data network, which in one example may comprise an Internet Protocol (IP) network (e.g., an IP Multimedia Subsystem (IMS) network), an asynchronous transfer mode (ATM) network), a cellular network (e.g., 2G, 3G, and the like), a long term evolution (LTE) network, or the like. It should be noted that an IP network is broadly defined as a network that uses Internet Protocol to exchange data packets. Additional exemplary IP networks include Voice over IP (VoIP) networks, Service over IP (SoIP) networks, and the like.

In one example, the data network comprises a core network 126. In one example, core network 126 may combine core network components of a cellular network with components of a triple play service network; where triple play services include telephone services, Internet services, and television services to subscribers. For example, core network 126 may functionally comprise a fixed mobile convergence (FMC) network, e.g., an IP Multimedia Subsystem (IMS) network. In addition, core network 126 may functionally comprise a telephony network, e.g., an Internet Protocol/Multi-Protocol Label Switching (IP/MPLS) backbone network utilizing Session Initiation Protocol (SIP) for circuit-switched and Voice over Internet Protocol (VoIP) telephony services. Core network 126 may also further comprise an Internet Service Provider (ISP) network. In one embodiment, the core network 126 may include an application server (AS) 128 and a database (DB) 130. Although only a single application server 128 and a single database 130 are illustrated, it should be noted that any number of application servers and databases may be deployed. Furthermore, for ease of illustration, various additional elements of core network 126 are omitted from FIG. 1, including switches, routers, firewalls, web servers, and the like.

The core network 126 may be in communication with one or more wireless access networks 132 and 134. Either or both of the access networks 132 and 134 may include a radio access network implementing such technologies as: global system for mobile communication (GSM), e.g., a base station subsystem (BSS), or IS-95, a universal mobile telecommunications system (UMTS) network employing wideband code division multiple access (WCDMA), or a CDMA3000 network, among others. In other words, either or both of the access networks 132 and 134 may comprise an access network in accordance with any "second generation" (2G), "third generation" (3G), "fourth generation" (4G), Long Term Evolution (LTE), or any other yet to be developed future wireless/cellular network technology including "fifth generation" (5G) and further generations. The operator of core network 126 may provide a data service to subscribers via access networks 132 and 134. In one embodiment, the access networks 132 and 134 may all be different types of access networks, may all be the same type of access network, or some access networks may be the same type of access network and other may be different types of access networks. The core network 126 and the access networks 132 and 134 may be operated by different service providers, the same service provider or a combination thereof.

In one example, the access network 132 may be in communication with one or more user endpoint devices (also referred to as "endpoint devices" or "UE"), including the system 100. Similarly, the access network 134 may be in communication with one or more user endpoint devices, including a computing device 136 (e.g., a desk top computer, a lap top computer, a tablet computer, a smart phone, or any other computing device) that is operated by a healthcare provider. Access networks 132 and 134 may transmit and receive communications between respective UEs including the system 100 and computing device 136 and core network 126 relating to communications with web servers, AS 128, and/or other servers via the Internet and/or other networks, and so forth.

In one example, the system 100 may have cellular access capabilities (e.g., via the modem 116), while the other UE's (including the computing device 136) may have cellular and non-cellular access capabilities and may further have wired communication and networking capabilities (e.g., such as a desktop computer).

In one example, the application server 128 is configured to provide a web portal via which a healthcare provider, a patient, and/or any other authorized user may view data relating to the patient's medication adherence, as monitored by the system 100. For instance, the web portal may present a dashboard that is viewable on a remote computing device (such as computing device 136). The dashboard may present medication adherence data that is reported by the system 100 and stored in the database 130.

The database 130 stores the data relating to the patient's medication adherence, such as the medications prescribed to the patient, the number of doses of the medications consumed by the patient, and the times at which the doses were consumed. The database 130 may also store other patient information, such as doctor's notes, test results, medical history, allergies, and other data that may be relevant to the patient's medication adherence. This data may be stored in encrypted form to protect the patient's privacy.

Figure 6:
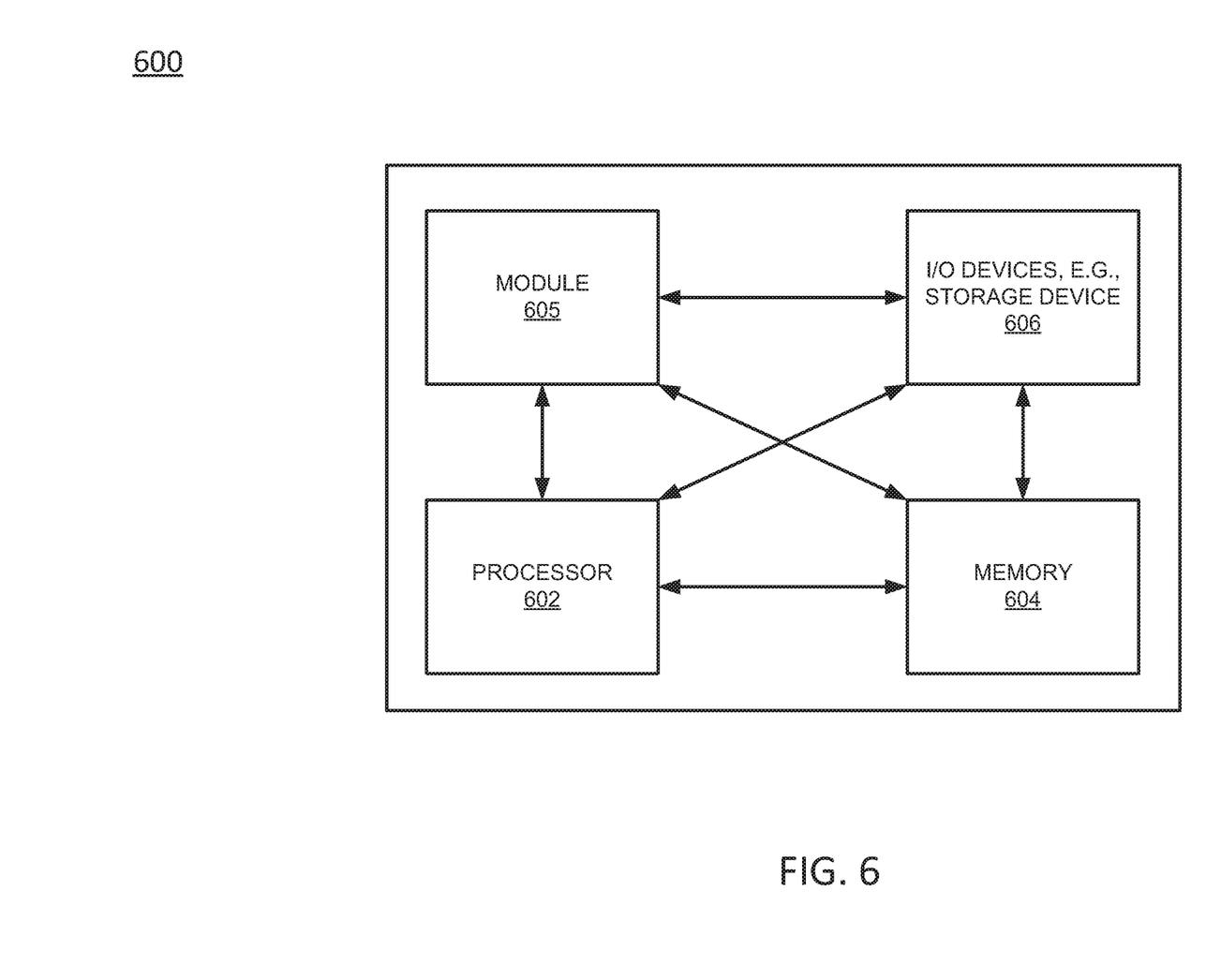
FIG. 6 depicts a high-level block diagram of a computing device specifically programmed to perform the functions described herein.

The application server 126 may comprise or be configured as a special purpose computer as illustrated in FIG. 6 and discussed below. It should also be noted that as used herein, the terms "configure" and "reconfigure" may refer to programming or loading a computing device with computer-readable/computer-executable instructions, code, and/or programs, e.g., in a memory, which when executed by a processor of the computing device, may cause the computing device to perform various functions. Such terms may also encompass providing variables, data values, tables, objects, or other data structures or the like which may cause a computer device executing computer-readable instructions, code, and/or programs to function differently depending upon the values of the variables or other data structures that are provided.

Those skilled in the art will realize that the data network illustrated in FIG. 1 has been simplified. For example, the data network may include other network elements (not shown) such as border elements, routers, switches, policy servers, security devices, a content distribution network (CDN) and the like. The data network may also be expanded by including additional endpoint devices, access networks, network elements, application servers, etc. without altering the scope of the present disclosure.

Thus, the dock 102 and unit dose packaging 104 of the system 100 work together to monitor when medication is dispensed from the unit dose packaging 104. In practice, when the medication is administered by a healthcare provider (e.g., by a doctor or a pharmacist), the healthcare provider may insert the unit dose packaging 104 into the dock 102 and activate or register the system 100 with a monitoring service over a data network. In one example, the healthcare provider may also reversibly lock the dock 102, so that the unit dose packaging 104 cannot be removed from the dock 102 by the patient. The entire system 100 may then be turned over to the patient. As the patient consumes the medication, the system 100 will monitor the consumption, record it in memory, and/or report it to the monitoring service, e.g., using the cellular modem 116 to connect to the data network. The monitoring service may provide feedback to the system 100 as necessary, e.g., using the cellular modem to connect to the dock 102 (where the feedback may, in turn, be displayed on the display 118 of the dock 102) to encourage the patient's adherence to the medication regimen. When the patient has completed the medication regimen, the system 100 may be returned to the healthcare provider. The healthcare provider may remove the unit dose packaging 104 from the dock 102 (possibly unlocking the dock 102 to access the unit dose packaging 104), so that the dock 102 can be reused with a new (e.g., full) unit dose packaging 104 when needed.

Figure 2:
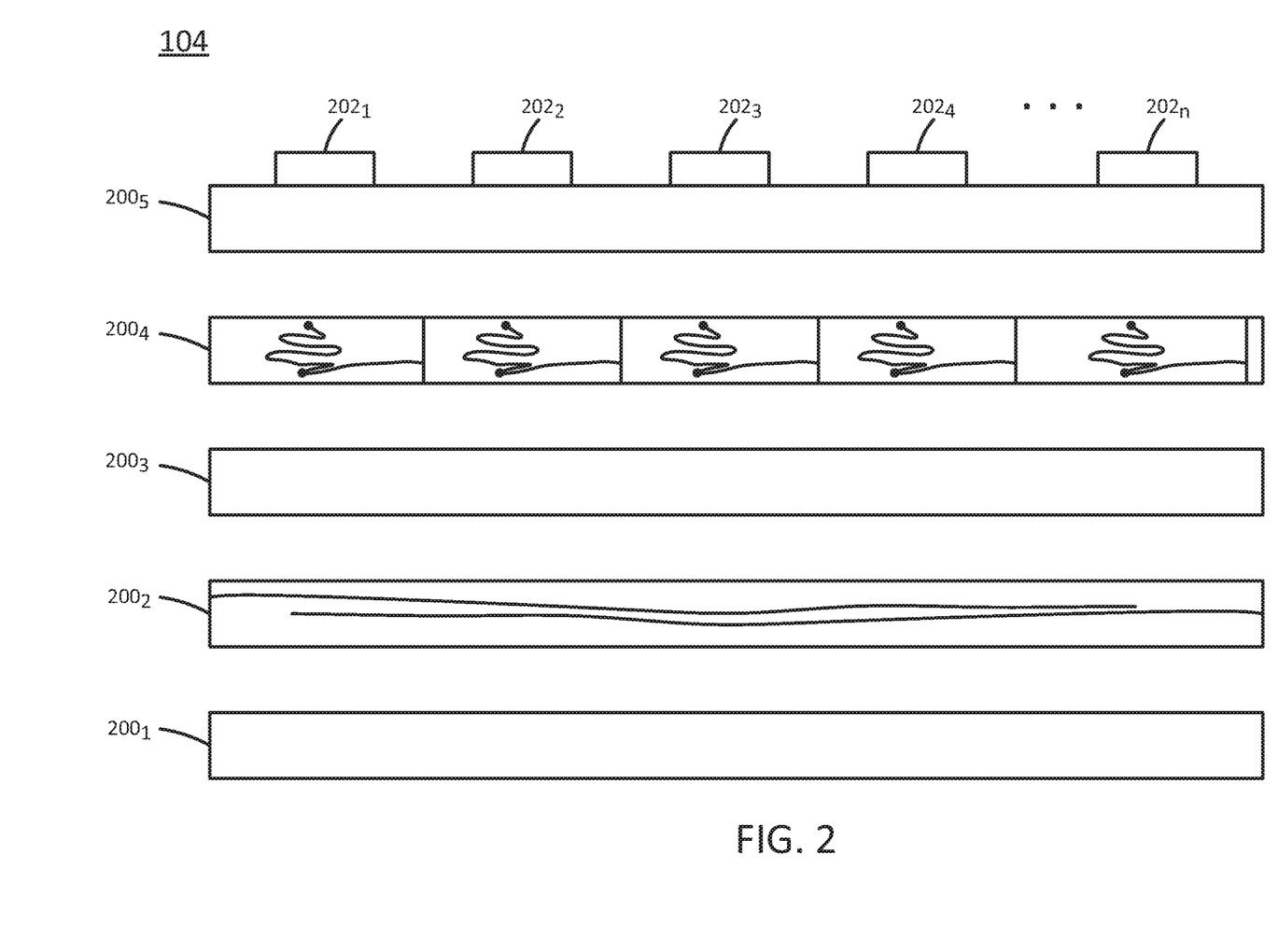
FIG. 2 illustrates an exploded view of the unit dose packaging illustrated in FIG. 1.

FIG. 2 illustrates an exploded view of the unit dose packaging 104 illustrated in FIG. 1. As illustrated in FIG. 2, the unit dose packaging 104 includes a plurality of layers $200_1$-$200_5$ (hereinafter individually referred to as a "layer 200" or collectively referred to as "layers 200"). The layers may be formed as part of a form-fill-seal process, e.g., in which the unit dose packaging 104 is created from rolls of flat sheet or film, filled with the doses of the medication, and closed (sealed) on the same equipment.

In one example, the first layer $200_1$ is a first dielectric layer. The first layer $200_1$ may therefore comprise a sheet of a dielectric, or insulating, material. The second layer $200_2$ may be formed directly on the first layer $200_1$ and may comprise a first conductive layer. The second layer $200_2$ may include traces of a conductive ink (e.g., silver, copper, or the like) that connect specific locations on the unit dose packaging 104 to a common contact portion, such as contact portion 108 of FIG. 1.

The third layer $200_3$ may be formed directly on the second layer $200_2$ and may comprise a second dielectric layer that functions as a crossover dielectric barrier layer. Thus, the third layer $200_3$ may comprise a sheet of a dielectric, or insulating, material. The fourth layer $200_4$ may be formed directly on the third layer $200_3$ and may comprise a second conductive trace layer. The fourth layer $200_4$ may include traces of a conductive ink (e.g., silver, copper, or the like) that form portions of a conductive trace circuit that can be broken when a pocket $202_1$-$202_n$ of the unit dose packaging 104 is opened.

The fifth layer $200_5$ may be formed directly on the fourth layer $200_4$ and may comprise a third dielectric layer that functions as a finishing layer. Thus, the fifth layer $200_5$ may comprise a sheet of a dielectric, or insulating, material. The fifth layer $200_5$ may include a window or opening that exposes the contact portion 108 of the conductive trace circuit, so that the contact portion 108 is visible as it is in FIG. 1. In addition, the fifth layer $200_5$ may include at least one pocket $202_1$-$202_n$ (hereinafter individually referred to as a "pocket 202" or collectively referred to as "pockets 202") for containing an individual dose of a medication.

The fifth layer $200_5$ may further comprise a plurality of pockets $202_1$-$202_n$ (hereinafter individually referred to as a "pocket 202" or collectively referred to as pockets 202"). Each pocket 202 may contain a unit dose of a medication (e.g., an individual tablet or pill) and may be associated with a unique trace.

Although five layers 200 are illustrated in FIG. 2, it will be appreciated that the unit dose packaging 104 may comprise any number of layers. For instance, at least two of the layers 202 illustrated in FIG. 2 may be combined to form a single layer. In addition, other layers that are not illustrated in FIG. 2 may form part of the unit dose packaging 104, including backing layers to give the unit dose packaging 104 semi-rigid support, sealing layers to protect the unit dose packaging and its contents from external elements, and other layers. These other layers may be formed from thermo-formed plastics, paperboard, foil, and/or other materials.

Figure 4:
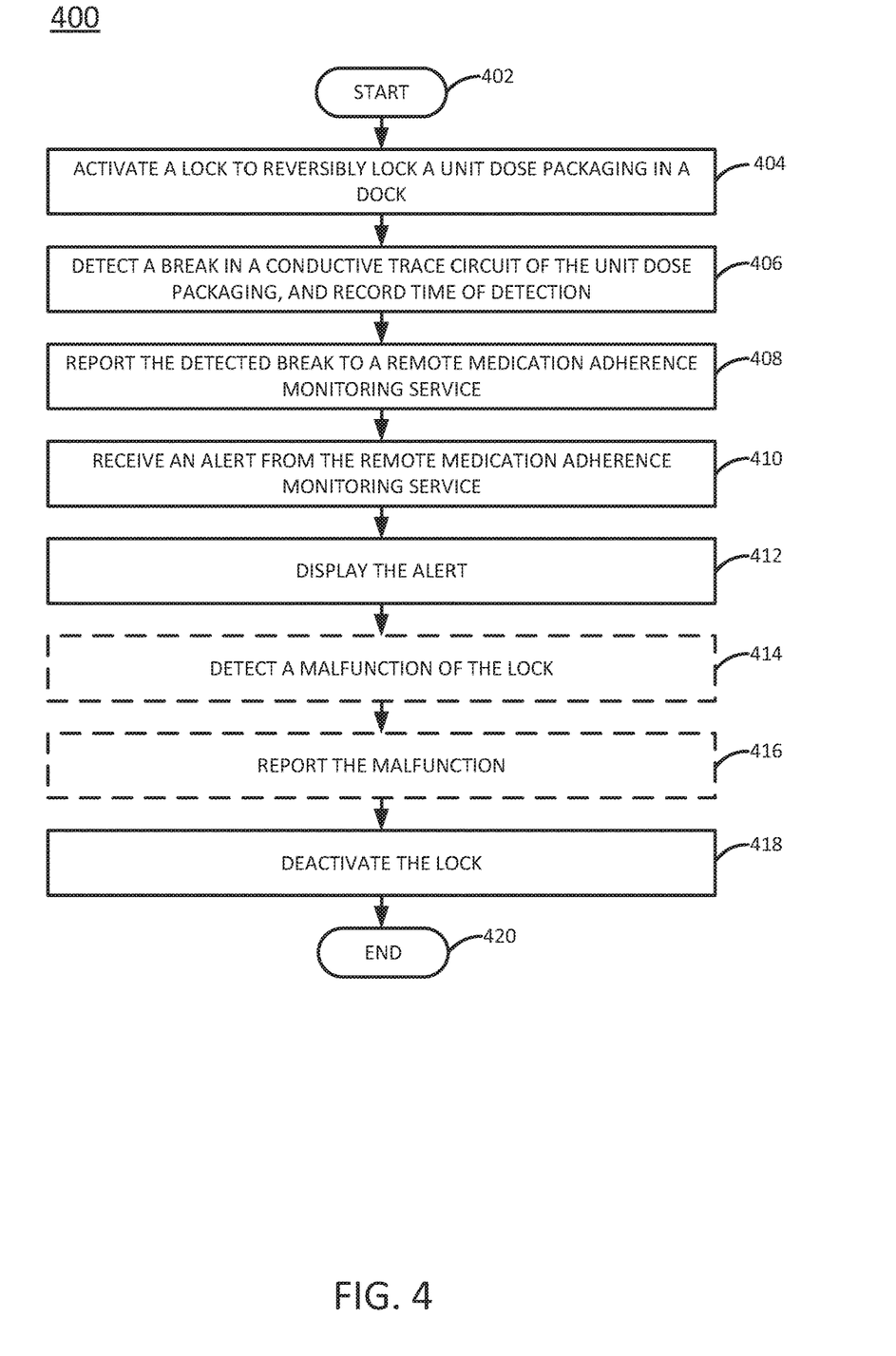
FIG. 4 illustrates a flowchart of a first example method for monitoring a patient's medication adherence.

FIG. 4 illustrates a flowchart of a first example method 400 for monitoring a patient's medication adherence. In one example, the method 400 may be performed by the dock 102 illustrated in FIG. 1. However, in other examples, the method 400 may be performed by another device. As such, any references in the discussion of the method 400 to the dock 102 of FIG. 1 (or any other elements of FIG. 1) are not intended to limit the means by which the method 300 may be performed.

In one example, operation of the method 400 assumes that a unit dose packaging such as the unit dose packaging 104 of FIG. 1 has been inserted into the dock 102, and that the system 100 has subsequently been registered, e.g., with the AS 128, as described above.

The method 400 begins in step 402. In step 404, a lock is activated to reversibly lock a unit dose packaging in a dock. In this case, the lock may be activated electronically (e.g., using a command or password, possibly issued by an authenticated device). The lock may be activated under the instruction of a healthcare provider, such as a pharmacist or a doctor. Activation of the lock should prevent the unit dose packaging from being removed from the dock without the proper key (e.g., command or password).

In step 406, a break in a conductive trace circuit that is embedded in a unit dose packaging is detected, and the time of detection is recorded. As described above, the set of contact pins 112 in the dock 102 may be in continuous contact with the conductive trace circuit (e.g., via contact portion 108) and may thus generate a signal to the processor 114 of the dock 102 when a break in the conductive trace circuit occurs.

In step 408, the detected break in the conductive trace circuit is reported to a remote medication adherence monitoring service. As discussed above, in one example, a cellular modem 116 of the dock 102 may enable the dock 102 to communicate with a remote application server (e.g., AS 128) and/or remote database (e.g., DB 13) in the cloud.

In step 410, an alert is received from the remote service. The alert may be generated in response to the reporting of the detected break in step 408. In other examples, the alert may be generated when a reported break is not reported within an expected range of times. As discussed above, the alert may comprise a reminder for a patient to take a scheduled dose of medication, a reminder to order a refill of the medication, an instruction for the patient to contact his or her healthcare provider, a reminder for a patient to take a specific action in connection with a consumption of the dose of the medication (e.g., taking the medication with food, or avoiding taking the medication in combination with other specific medications), or other feedback related to the patient's medication adherence.

In step 412, the alert is displayed to the patient, e.g., via a display 118 of the dock 102. For instance, the alert may be displayed as string of text (e.g., "Don't forget to take your next dose of Medication A with food by 12:00 PM)", an image or animation (e.g., an image of a pill), or a combination of text and images. In further examples, the alert may include an audible alert (e.g., a beep or a tone), a haptic alert (e.g., a vibration), or another type of alert.

In step 414 (illustrated in phantom), a malfunction of the lock may be detected. The malfunction may be the result of damage to the lock. In one example, the malfunction of the lock may be detected through an unauthorized or unexpected opening of the dock housing. For instance, it may be detected that the housing has been opened, but that the patient has not yet completed the prescribed regimen (e.g., has not yet consumed all expected doses contained in the unit dose packaging).

In step 416 (illustrated in phantom), the lock malfunction may be reported to the remote medication adherence monitoring service. The remote medication adherence monitoring service may, in turn, notify a healthcare provider of the lock malfunction (e.g., the same healthcare provider who caused the lock to be activated).

In step 418, the lock may be deactivated. Similar to activation of the lock, deactivation of the lock may be performed electronically (e.g., using a command or password, possibly issued by an authenticated device). and may be performed under the instruction of a healthcare provider, such as a pharmacist or a doctor. For instance, a pharmacist may deactivate the lock when a patient returns the dock along with the empty unit dose packaging. Deactivation of the lock allows the empty unit dose packaging to be removed from the dock, so that a new (e.g., full) unit dose packaging can be inserted into the dock, either for the same patient (if the patient is continuing the medication regimen) or for a new patient.

The method 400 ends in step 420. In practice, the method 400 may repeat many times as the patient consumes the medication according to the prescribed regimen. For instance, the method 400 may repeat until the unit dose packaging is empty, until the dock is deactivated by the healthcare provider, or until another event occurs.

Figure 5:
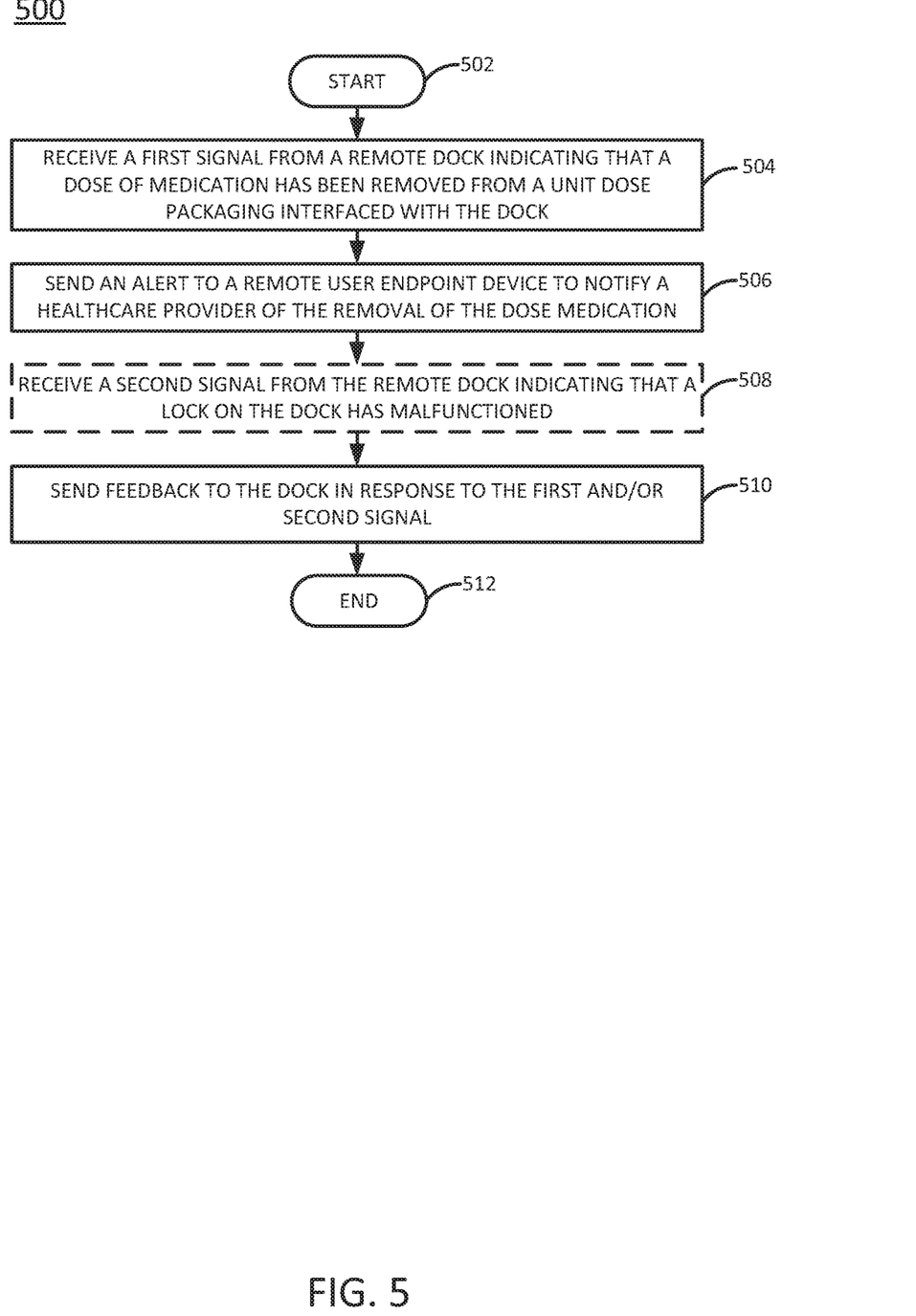
FIG. 5 illustrates a flowchart of a second example method for monitoring a patient's medication adherence.

FIG. 5 illustrates a flowchart of a second example method 500 for monitoring a patient's medication adherence. In one example, the method 500 may be performed by the application server 128 illustrated in FIG. 1. However, in other examples, the method 500 may be performed by another device. As such, any references in the discussion of the method 500 to the AS 128 of FIG. 1 (or any other elements of FIG. 1) are not intended to limit the means by which the method 500 may be performed.

In one example, operation of the method 500 assumes that a unit dose packaging such as the unit dose packaging 104 of FIG. 1 has been inserted into a dock such as the dock 102 of FIG. 1 (and that the dock 102 has potentially been locked to prevent removal of the unit dose packaging 104), and that the system 100 has subsequently been registered with the AS 128, as described above.

The method 500 begins in step 502. In step 504, a first signal is received, e.g., via a data network, from a dock that is interfaced with a unit dose packaging. In one example, the first signal indicates that a dose of a medication has been removed from the unit dose packaging. The first signal may further indicate the time at which the dose was removed.

In step 506, an alert is sent to a user endpoint device, such computing device 136, to notify a healthcare provider that the dose of the medication was removed. The alert may also specify the time at which the dose was removed. In one example, the alert may be sent directly to a dashboard or GUI that is presented on the user endpoint device. In another example, the alert may comprise an email, a text message, or the like. The email or text message may contain the information about the dose of medication that was removed. Alternatively, the email or text message may instruct the recipient to log into a web portal to access the information about the dose of medication that was removed.

In step 508 (illustrated in phantom), a second signal is received from the dock. In one example, the second signal indicates that a lock on the dock has malfunctioned. For example, the second signal may indicate that the dock was opened at an unauthorized or unexpected time (e.g., before the patient has consumed all expected doses contained in the unit dose packaging).

In step 510, feedback is sent to the dock. The feedback may be generated automatically in response to the first and/or second signal, e.g., in accordance with a set of predefined rules (e.g., "Send reminder to take dose of medication A if no signal indicating removal of dose is received by 12:00 PM" or "Send instruction to return dock to health care provider for maintenance if signal indicating lock malfunction is received") or may be sent in response to a healthcare provider providing feedback, e.g., via the web portal (e.g., "Don't forget to take Medication A with food").

The method 500 ends in step 512. In practice, the method 500 may repeat many times as the patient consumes the medication according to the prescribed regimen. For instance, the method 500 may repeat until the unit dose packaging is empty, until the dock is deactivated by the healthcare provider, or until another event occurs.

Although not expressly specified above, one or more steps of the methods 400 and 500 may include a storing, displaying, and/or outputting step as required for a particular application. In other words, any data, records, fields, and/or intermediate results discussed in the method can be stored, displayed and/or outputted to another device as required for a particular application. Furthermore, operations, steps, or blocks in FIGS. 4 and 5 that recite a determining operation or involve a decision do not necessarily require that both branches of the determining operation be practiced. In other words, one of the branches of the determining operation can be deemed as an optional step. Furthermore, operations, steps or blocks of the above described method(s) can be combined, separated, and/or performed in a different order from that described above, without departing from the examples of the present disclosure.

FIG. 6 depicts a high-level block diagram of a computing device specifically programmed to perform the functions described herein. For example, any one or more components or devices illustrated in FIG. 1 or described in connection with the methods 400 and 500 may be implemented as the system 600. For instance, the dock 102 of FIG. 1 (such as might be used to perform the method 400) could be implemented as illustrated in FIG. 6. In another example, the application server 128 of FIG. 1 (such as might be used to perform the method 500) could be implemented as illustrated in FIG. 6.

As depicted in FIG. 6, the system 600 comprises a hardware processor element 602, a memory 604, a module 605 for monitoring a patient's medication adherence, and various input/output (I/O) devices 606.

The hardware processor 602 may comprise, for example, a microprocessor, a central processing unit (CPU), or the like. The memory 604 may comprise, for example, random access memory (RAM), read only memory (ROM), a disk drive, an optical drive, a magnetic drive, and/or a Universal Serial Bus (USB) drive. The module 605 for monitoring a patient's medication adherence may include circuitry and/or logic for performing special purpose functions relating to monitoring, reporting, and/or providing feedback related to medication adherence for a specific patient The input/output devices 606 may include, for example, storage devices (including but not limited to, a tape drive, a floppy drive, a hard disk drive or a compact disk drive), a receiver, a transmitter, a display, a speaker, a haptic feedback mechanism, an output port, or a user input device (such as a keyboard, a keypad, a mouse, a touch screen and the like).

Although only one processor element is shown, it should be noted that the general-purpose computer may employ a plurality of processor elements. Furthermore, although only one general-purpose computer is shown in the Figure, if the method(s) as discussed above is implemented in a distributed or parallel manner for a particular illustrative example, i.e., the steps of the above method(s) or the entire method(s) are implemented across multiple or parallel general-purpose computers, then the general-purpose computer of this Figure is intended to represent each of those multiple general-purpose computers. Furthermore, one or more hardware processors can be utilized in supporting a virtualized or shared computing environment. The virtualized computing environment may support one or more virtual machines representing computers, servers, or other computing devices. In such virtualized virtual machines, hardware components such as hardware processors and computer-readable storage devices may be virtualized or logically represented.

It should be noted that the present disclosure can be implemented in software and/or in a combination of software and hardware, e.g., using application specific integrated circuits (ASIC), a programmable logic array (PLA), including a field-programmable gate array (FPGA), or a state machine deployed on a hardware device, a general purpose computer or any other hardware equivalents, e.g., computer readable instructions pertaining to the method(s) discussed above can be used to configure a hardware processor to perform the steps, functions and/or operations of the above disclosed method(s). In one example, instructions and data for the present module or process 605 for monitoring a patient's medication adherence (e.g., a software program comprising computer-executable instructions) can be loaded into memory 604 and executed by hardware processor element 602 to implement the steps, functions or operations as discussed above in connection with the example methods 400 and 500. Furthermore, when a hardware processor executes instructions to perform "operations," this could include the hardware processor performing the operations directly and/or facilitating, directing, or cooperating with another hardware device or component (e.g., a co-processor and the like) to perform the operations.

The processor executing the computer readable or software instructions relating to the above described method(s) can be perceived as a programmed processor or a specialized processor. As such, the present module 605 for monitoring a patient's medication adherence (including associated data structures) of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. More specifically, the computer-readable storage device may comprise any physical devices that provide the ability to store information such as data and/or instructions to be accessed by a processor or a computing device such as a computer or an application server.

While various examples have been described above, it should be understood that they have been presented by way of example only, and not limitation. Thus, the breadth and scope of a preferred example should not be limited by any of the above-described example examples, but should be defined only in accordance with the following claims and their equivalents.

What is claimed is:

1. An apparatus, comprising:
   a set of contact pins to electrically engage a conductive trace circuit of a unit dose packaging and to generate a signal in response to a break in the conductive trace circuit;
   a housing containing the set of contact pins, wherein the housing is configured for removable insertion of the unit dose packaging; and
   a lock to reversibly lock the unit dose packaging in the housing.

2. The apparatus of claim 1, further comprising:
   a display to display information about the signal.

3. The apparatus of claim 1, wherein the set of contacts pins is positioned inside an opening in the housing.

4. The apparatus of claim 1, wherein the housing comprises:
   a first portion;
   a second portion; and
   at least one hinge connecting the first portion and the second portion, so that the first portion is rotatable relative to the second portion to open and close the housing.

5. The apparatus of claim 4, wherein an engagement of the lock prevents rotation of the first portion away from the second portion to open the housing.

6. The apparatus of claim 4, wherein a disengagement of the lock allows the first portion to rotate away from the second portion to open the housing.

7. The apparatus of claim 1, wherein the lock is activated and deactivated manually.

8. The apparatus of claim 1, wherein the lock is activated and deactivated electronically.

9. A method, comprising:
   receiving, by a processor of a server in a communications network, a signal from a dock, wherein the signal indicates a malfunction of a lock that reversibly interfaces a unit dose packaging with the dock; and
   sending, by the processor, feedback to the dock in response to the malfunction.

10. The method of claim 9, wherein the communications network is a cellular communications network.

11. The method of claim 9, wherein the server hosts a medication adherence monitoring service, and wherein the dock is registered with the medication adherence monitoring service upon the dock being interfaced with the unit dose packaging.

12. The method of claim 9, wherein the malfunction comprises an opening of the dock at an unexpected time.

13. The method of claim 12, wherein the unexpected time is a time prior to a patient consuming all expected doses of a medication contained in the unit dose packaging.

14. The method of claim 12, wherein the unexpected time is included in the signal.

15. The method of claim 9, wherein the feedback comprises an alert indicating that the dock should be returned to a healthcare provider for maintenance.

16. An apparatus, comprising:
 a processor of a server in a telecommunications network; and
 a computer-readable medium storing instructions which, when executed by the processor, cause the processor to perform operations, the operations comprising:
 receiving a signal from a dock, wherein the signal indicates a malfunction of a lock that reversibly interfaces a unit dose packaging with the dock; and
 sending feedback to the dock in response to the malfunction.

17. The apparatus of claim 16, wherein the server hosts a medication adherence monitoring service, and wherein the dock is registered with the medication adherence monitoring service upon the dock being interfaced with the unit dose packaging.

18. The apparatus of claim 16, wherein the malfunction comprises an opening of the dock at an unexpected time.

19. The apparatus of claim 18, wherein the unexpected time is a time prior to a patient consuming all expected doses of a medication contained in the unit dose packaging.

20. The apparatus of claim 16, wherein the feedback comprises an alert indicating that the dock should be returned to a healthcare provider for maintenance.

* * * * *